United States Patent [19]

Walsh

[11] Patent Number: 4,886,794

[45] Date of Patent: Dec. 12, 1989

[54] 4-[(α,α-DIARYL)-HYDROXYMETHYL]-1-PIPERIDINYLALKYL-CYCLIC CARBAMATE DERIVATIVES AS ALLERGIC RESPONSE INHIBITORS

[75] Inventor: David A. Walsh, Richmond, Va.

[73] Assignee: A. H. Robins Company, Incorporated, Richmond, Va.

[21] Appl. No.: 202,028

[22] Filed: Jun. 3, 1988

Related U.S. Application Data

[63] Continuation-in-part of Ser. No. 46,743, May 7, 1987, abandoned.

[51] Int. Cl.$^4$ .................. A61K 31/33; C07D 413/00; C07D 275/04; C07D 277/04
[52] U.S. Cl. .................. 514/211; 546/209; 546/193; 546/194; 544/96; 540/488; 540/454; 514/228.8; 514/318; 514/326
[58] Field of Search .................. 546/209, 193, 194; 544/96; 540/488, 454; 514/211, 228.8, 318, 326

[56] References Cited

U.S. PATENT DOCUMENTS 4,594,427  6/1986  Bonse et al. .................. 546/209

Primary Examiner—Mary C. Lee
Assistant Examiner—Robert C. Whittenbaugh

[57] ABSTRACT

4-[(α,α-Diaryl)-hydroxymethyl]-1-piperidinylalkylcyclic carbamate derivatives having the formula:

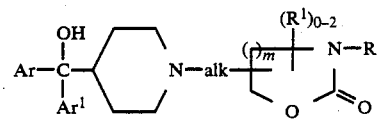

wherein;
R is hydrogen, loweralkyl, cycloalkyl, phenyl and substituted phenyl;
Ar and Ar$^1$ are phenyl, substituted phenyl or pyridinyl;
alk is a straight or branched hydrocarbon chain;
R$^1$ is loweralkyl substituted for hydrogen on a ring carbon.

The compounds are useful antihistamines and in controlling allergic response.

60 Claims, No Drawings

4-[(α,α-DIARYL)-HYDROXYMETHYL]-1-PIPERIDINYLALKYL-CYCLIC CARBAMATE DERIVATIVES AS ALLERGIC RESPONSE INHIBITORS

This application is a continuation-in-part application of copending U.S. patent application Ser. No. 046,743, filed May 7, 1987 now abandoned.

BACKGROUND OF THE INVENTION

1. Field of Invention.

This invention relates to novel cyclic carbamate derivativese having ring carbon substitution by a 4-[α,α-diaryl-hydroxymethyl]-1-piperidinylalkyl radical. The cyclic carbamate derivatives encompassed by the invention are those of the 2-oxazolidinones, the 1,3-oxazin-2-ones, the 1,3-oxazepin-2-ones, and the 1,3-oxazocin-2-ones. The compounds are useful in methods countering the effects of histamine already released and in combating allergic responses in a living animal body in need thereof and pharmaceutical compositions therefor. More specifically the methods employ the compounds inhibiting Type I allergic response (Gell & Coombs Classification of Immune Responses) and in preventing release of histamine as well as antagonizing end organ effects of mediators involved in the immediate hypertensivity response and as such are useful in treating allergic phenomena which includes asthma, rhinitis, atopic dermatitis, chronic hives, allergic conjunctivitis, and the like, as well as the symptomatic effects of the allergic phenomena. These pharmacological activities, i.e., antihistaminic and antiallergenic being complementary in effect when needed.

2. Information Disclosure Statement

4-[Bis(aryl)hydroxymethyl]piperidines used in synthesis are disclosed in U.S. Pat. Nos. 3,956,296; 4,032,642; and in copending application Ser. No. 811,799, filed 12/20/85 now U.S. Pat. No. 4,810,713. N-Substituted-haloalkyloxazolidin-2-ones and 1,3-oxazin-2-ones used in synthesis have been disclosed in U.S. Pat. No. 3,423,418 and in the following publications: J. MED. CHEM. 16, 1124–1128 (1973); J. ORG. CHEM. 35, 4100–4103 (1970); and J. PHARM. SCI. 58, 362–364 (1969). A search of the literature has not revealed a combination of these foregoing moieties to give the subject compounds of this invention.

OBJECTS AND SUMMARY OF THE INVENTION

The novel cyclic carbamate derivatives of this invention useful in treating allergy in animals are substituted on one of the ring carbon atoms by a 4-[(bis-aryl)hydroxymethyl]-1-piperidinylalkyl radical and are represented by the formula:

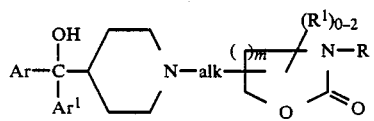

Formula I wherein;
R is selected from hydrogen, loweralkyl, cycloalkyl, phenyl,

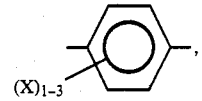

phenyl-loweralkyl or

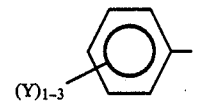

loweralkyl; Ar and $Ar^1$ are selected from phenyl,

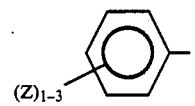

or 2, 3 or 4-pyridinyl radicals;
alk is a straight or branched hydrocarbon chain containing 1-8 carbon atoms;
$R^1$ is loweralkyl substituted for hydrogen on a ring carbon;
m is 1 to 4;
X, Y, and Z are selected from halogen, loweralkyl, loweralkoxy, or trifluoromethyl, and when more than 1 may be the same or different; optical isomers thereof and the pharmaceutically acceptable acid addition salts thereof.

In the further definition of symbols in the formulas hereof and where they appear elsewhere throughout this specification and claims, the terms have the following significance.

The term "loweralkyl" includes straight and branched chain hydrocarbon radicals of up to eight carbon atoms inclusive and is exemplified by such groups as methyl, ethyl, propyl, isopropyl, butyl, isobutyl, tertiary butyl, amyl, isoamyl, hexyl, heptyl, octyl, and the like. "Loweralkoxy" has the formula -O-loweralkyl.

The term "cycloalkyl" as used herein includes primarily cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The terms "halogen" or "halo" include chlorine, bromine, fluorine and iodine radicals, preferably chlorine, bromine and fluorine radicals.

The "alk" straight or branched connecting hydrocarbon chain containing 1-8 carbons is exemplified by methylene (—CH₂—), ethylene (—CH₂CH₂—), propylene (—CH₂CH₂CH₂—), ethylidene

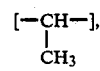

1,2-propylene

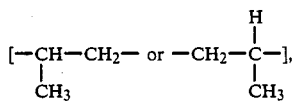

isopropylidene

or 1,3-butylene

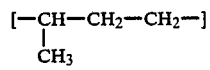

and the like;

Pharmaceutically acceptable acid addition salts are those salts formed with the free base compounds of Formula I with any acid which is physiologically compatible in warm blooded animals, such salts being formed either by strong or weak acids. Representative of strong acids are hydrochloric, hydrobromic, sulfuric and phosphoric acids. Representative of weak acids are fumaric, maleic, succinic, oxalic, hexamic, and the like, and hydrates or solvates thereof.

The primary screening method used to detect antiallergy properties of the compounds of Formula I is a modification of the procedure of R. R. Martel and J. Klicius, INTERN. ARCH. ALLERGY APPL. IMMUNOLOGY, Vol. 54 pp 205–209 (1977) which measures the effect of oral administration of the compound on the volume of a rat paw which was previously injected with anti-egg albumin serum and is described under Pharmacology Methods hereinbelow.

A method of studying potency in preventing guinea pig anaphylaxis relative to known antiallergy drugs is also described hereinbelow.

The Gell and Coombs Classification of Immune Responses referred to hereinabove is well known in the art and is described in ESSENTIAL IMMUNOLOGY, 3rd Ed. (1977) (Blackwell Scientific Publications) printed by William Clowes and Sons, Limited, London, Beccles and Colchester.

It is therefore a primary object of the present invention to provide novel 4-[($\alpha,\alpha$-diaryl)hydroxymethyl]-1-piperidinylalkyl-cyclic carbamate derivatives useful in combating histamine and allergic responses in living animals and pharmaceutical compositions therefor.

Additional objects and advantages of the present invention will be apparent to one skilled in the art and others will become apparent from the following description of the best mode of carrying out the present invention and in the appended claims.

DETAILED DESCRIPTION OF THE INVENTION

Compounds of Formula I are prepared by the method illustrated in the following schematic equation in Chart I.

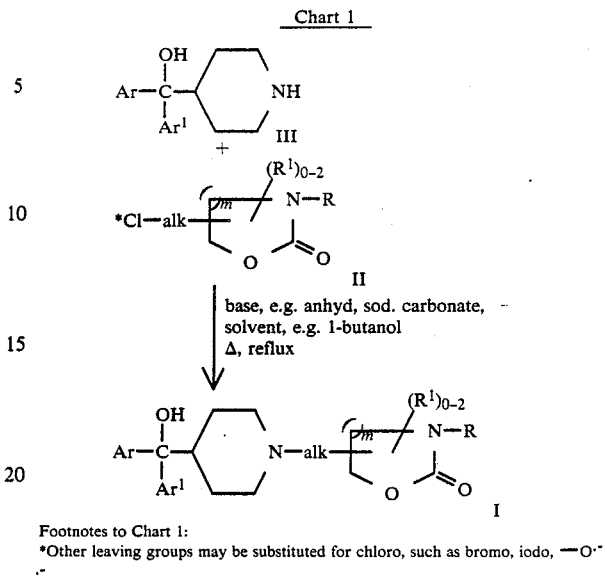

Footnotes to Chart 1:
*Other leaving groups may be substituted for chloro, such as bromo, iodo, —O·⁻

Ar, Ar$^1$, R, R$^1$, alk and m have values as defined under Formula I above.

Generally, compounds of Formulas II and III, base, iodide catalyst, and solvent such as butanol are heated together for a period of time, usually several hours, at about 100° C. or until reaction is complete. The mixture is then concentrated under reduced pressure and the residue is partitioned between water and a suitable solvent for the free base, e.g., benzene. The benzene layer is separated, dried and concentrated and the product is isolated usually, but not always, as an acid addition salt.

Certain of the starting oxazolidinones and 2H-1,3-oxazin-2-ones were prepared by a rearrangement method described in U.S. Pat. No. 3,419,559 for the oxazolidinones according to the following reaction scheme:

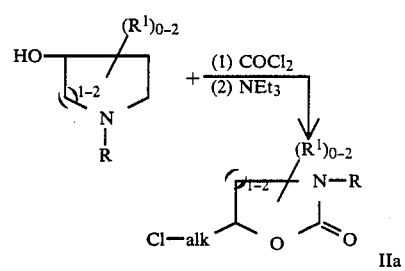

Other references pertinent to the preparation of the starting 2-oxazolidinones and 2H-1,3-oxazin-2-ones are as follows: Fielden, M. et al., J. MED. CHEM. 16, 1124–1128 (1973); J. ORG. CHEM. (Sci. & Biol.) 35, 4100–4103 (1970); Darling & Beauchamp, J. PHARM. SCI. 58, 362–364 (1969); and U.S. Pat. No. 3,423,418.

The starting 3-pyrrolidinols wherein R$^1$ radicals are present may be obtained by the procedure of Ryan et al., J. ORG. CHEM. 27, 2901–2905 (1962) or according to U.S. Pat. No. 2,830,997 and other sources cited therein.

A more general method of preparation for cyclic carbamate starting materials is represented by the following reaction scheme:

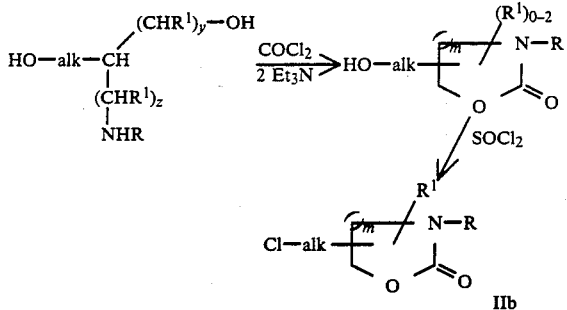

$y=0-4$; $z=0-4$ and the sum of y and z does not exceed 4.

In the instance where mixtures result, the compounds may be separated by chromatography.

Compounds of Formula IIa and IIb are encompassed by Formula II.

Compounds of Formula I have a chiral center in the cyclic carbamate ring at the site of the carbon carrying the side chain and therefore there is potential for separation of the enantiomers (optical isomers) or for synthesis of the enantiomers using already resolved starting chemicals or chemical intermediates. R and S enantiomers of the 2-oxazolidinone derivatives were prepared (see Examples 4 and 5 hereinbelow) starting with R and S enantiomers of 1-methyl-3-pyrrolidinol (preparation of optically active pyrrolidinols described in U.S. Pat. No. 4,592,866) and both isomers were found to be pharmacologically active for the activities of anti-allergenic and anti-histaminic methods of the invention. All of the enantiomers of compounds of Formula I may be prepared starting with optically active amino alcohols in the more general method outlined above for preparing compounds of Formula IIb.

The free bases of acid addition salts of starting materials and end products are prepared by conventional means by partitioning the salt between dilute aqueous alkali metal base and a solvent such as methylene chloride followed by evaporation of the solvent layer.

The following preparations and examples are given by way of illustration only and are not to be construed as limiting.

PREPARATION 1

5-(2-Chloroethyl)-3-(1-methylethyl)-2-oxazolidinone

To a cold (ice bath) solution of 98.5 g (10 mole) of phosgene in 500 ml of methylene chloride was added dropwise a solution of 129.2 g (1.0 mole) of 1-isopropyl-3-pyrrolidinol in 250 ml of methylene chloride at such a rate that the temperature did not exceed 10° C. After addition was complete, the mixture was stirred in the cold for 1 hr and then treated dropwise with 140 ml (101 g, 1.0 mole) of triethylamine at such a rate that the temperature did not exceed 25° C. The mixture was stirred at ambient temperature for 3 hr and then treated with 500 ml of 1N hydrochloric acid solution. The layers were separated and the organic layer was washed successively with 500 ml of a 1N hydrochloric acid solution, 500 ml of a 4% sodium hydroxide solution and 500 ml of brine, dried over sodium sulfate and concentrated under reduced pressure to give a brown oil as residue. The oil was subjected to vacuum distillation to yield 134.9 g (70%) of yellow oil, b.p. 110° C. at 0.2 mm.

Analysis: Calculated for $C_8H_{14}ClNO_2$: C,50.14; H,7.36; N,7.31. Found: C,49.64; H,7.43; N,7.30.

PREPARATION 2

5-(2-Chloroethyl)-3,4-dimethyl-2-oxazolidinone

To a chloroform solution containing 68.12 g (0.7 mole) of phosgene at 0°–10° C. was added 80 g (0.7 mole) of 1,2-dimethyl-3-pyrrolidinol at a rate to maintain the temperature below 10° C. The reaction mixture was allowed to stir at room temperature overnight. The mixture was cooled in an ice bath and 100 ml of triethylamine was added dropwise maintaining the temperature below 10° C. The mixture was extracted in order with water, 3N hydrochloric acid solution, 3N sodium hydroxide solution and again with water. The chloroform layer was dried over anhydrous sodium sulfate and evaporated to yield 110 g of dark amber oil which was distilled at 113°–118° C. at 0.05 mm to give 80 g (64.8%) of pale yellow oil, $n^{22}=1.4796$.

Analysis: Calculated for $C_7H_{12}ClNO_2$: C,47.33; H,6.81; N,7.89; Cl,19.96. Found: C,47.40; H,6.88; N,7.94; Cl,20.02.

PREPARATION 3 (a to l)

Utilizing the procedures of Preparations 1, 2 and of U.S. Pat. No. 3,419,559, the following were prepared:
(a) 5-(2-chloroethyl)-3-ethyl-2-oxazolidinone,
(b) 5-(2-chloroethyl)-3-methyl-2-oxazolidinone,
(c) 5-(2-chloroethyl)-3-benzyl-2-oxazolidinone,
(d) 5-(2-chloroethyl)-3-phenyl-2-oxazolidinone,
(e) 5-(2-chloroethyl)-3-(1-butyl)-2-oxazolidinone,
(f) 5-(1-methyl-2-chloroethyl)-3-methyl-2-oxazolidinone,
(g) 5-(3-chloropropyl)-3-methyl-2-oxazolidinone,
(h) 5-(4-chlorobutyl)-3-methyl-2-oxazolidinone,
(i) 5-(2-chloroethyl)-3(4methoxyphenyl)-2-oxazolidinone,
(j) 5-(2-chloroethyl)-3-phenyl-2-oxazolidinone,
(k) 5-(2-chloroethyl)-3-(4-methylphenyl)-2-oxazolidinone,
(l) 5-(2-chloroethyl)-3-(3-chlorophenyl)-2-oxazolidinone.

PREPARATION 4

3-Benzyl-5-chloromethyl-2-oxazolidinone

A solution of 20 g (0.1 mole) of 3-benzyl-5-hydroxymethyl-2-oxazolidinone and 24 g (0.2 mole) of sulfonyl chloride in chloroform was refluxed for 3 hr. The reaction mixture was dried over anhydrous sodium sulfate, concentrated and subjected to distillation to give 18.2 g (81%) liquid, b.p. 176°–178° C. at 0.1 mm.

Analysis: Calculated for $C_{11}H_{12}ClNO_2$: C,58.55; H,5.36; N,6.21. Found: C,58.30; H,5.24; N,6.27.

PREPARATION 5

5-(Chloromethyl)-3-methyl-2-oxazolidinone

A solution of 64.5 g (0.5 mole) of 1,3-dichloro-2-propanol in 200 ml of methylene chloride was treated with 28.5 g (0.5 mole) of methyl isocyanate and a few drops of triethylamine and allowed to stir at ambient temperature overnight. The solution was concentrated and the residue was dissolved in 200 ml of 95% ethanol and treated with a solution of 33.6 g (0.6 mole) of potassium hydroxide in 300 ml of 95% ethanol. The mixture was stirred at ambient temperature for 3.5 hr and then concentrated. The residue was partitioned between 250 ml of benzene and 100 ml of water. The organic layer was washed successively with 50 ml of a 2N hydrochloric acid solution and 100 ml of brine, dried over anhydrous sodium sulfate and concentrated to give 50.5 g of oil as residue. The oil was subjected to vacuum distillation to yield 36.9 g (49%) of clear oil, b.p. 131°–133° C. at 0.3 mm.

Analysis: Calculated for $C_5H_8ClNO_2$: C,40.15; H,5.39; N,9.36. Found: C,38.77; H,5.39; N,9.08.

PREPARATION 6

S-(−)-5-(2-Chloroethyl)-3-methyl-2-oxazolidinone

To a solution of 102.9 g (1.04 mole) of phosgene in 500 ml of methylene chloride was added dropwise a solution of 105.3 g (1.04 mole) of S(+)-1-methyl-3-pyrrolidinol, (~8% R-isomer) in 250 ml of methylene chloride at such a rate that the internal temperature did not exceed 15° C. After the addition was complete, the solution was stirred at ice bath temperature for 0.75 hr and then treated dropwise with 145 ml (105 g, 1.04 mole) of triethylamine at such a rate that the temperature did not exceed 25° C. The mixture was stirred at ambient temperature for 3 hr and then treated with a solution of 50 ml of concentrated hydrochloric acid in 500 ml of water. The layers were separated and the organic layer was washed once with 500 ml of a 4% sodium hydroxide solution, dried over anhydrous sodium sulfate and concentrated under reduced pressure to give an oil as residue. The oil was subjected to vacuum distillation to yield 99.3 g (61%) of clear oil, b.p. 128° C. at 0.5 mm, ($[\alpha]_D^{25}= -58.3°$ [methanol]).

Analysis: Calculated for $C_6H_{10}ClNO_2$: C,44.04; H,6.16; N,8.56. Found: C,43.51; H,6.24; N,8.44.

PREPARATION 7

R-(+)-5-Chloroethyl)-3-methyl-2-oxazolidinone

To a solution of 133.8 g (1.35 mole) of phosgene in 650 ml of methylene chloride was added dropwise a solution of 136.8 g (1.35 mole) of R(−)-1-methyl-3-pyrrolidinol, (~7% S-isomer) in 300 ml of methylene chloride at such a rate that the internal temperature did not exceed 15° C. After the addition was complete, the solution was stirred at ice bath temperatures for 0.75 hr and then treated dropwise with 188 ml (136.5 g, 1.35 mole) of triethylamine at such a rate that the temperature did not exceed 25° C. The mixture was stirred at ambient temperature overnight and then treated with a solution of 50 ml of concentrated hydrochloric acid in 500 ml of water. The layers were separated and the organic layer was washed once with 500 ml of a 4% sodium hydroxide solution, dried over sodium sulfate and concentrated under reduced pressure to give an oil as residue. The oil was subjected to vacuum distillation to yield 136.6 g (83%) of clear oil, b.p. 123°–126° C. at 0.5 mm, ($[\alpha]_D^{25}$ +71.1° C. (methanol)).

Analysis: Calculated for $C_6H_{10}ClNO_2$: C,44.04; H,6.16; N,8.56. Found: C,43.19; H,6.21; N,8.38.

PREPARATION 8

6-(2-Chloroethyl)tetrahydro-3-methyl-2H-1,3-oxazin-2-one

To a cold (ice bath) solution of 85.8 g (0.868 mole) of phosgene in 500 ml of methylene chloride was added dropwise a solution of 100 g (0.868 mole) of 4-hydroxy-1-methylpiperidine in 250 ml of methylene chloride at such a rate that the internal temperature did not exceed 12° C. A crystalline solid precipitated during addition. The mixture was stirred in the cold for 1 hr after addition was complete and then 120.8 ml (87.7 g, 0.868 mole) of triethylamine was added dropwise at such a rate that the internal temperature did not exceed 25° C. The mixture was stirred at ambient temperature overnight and then diluted with 500 ml of toluene. The methylene chloride was removed by distillation and the resultant mixture was heated at reflux for 2 hr. The mixture was cooled and treated with 500 ml of 1N hydrochloric acid. The layers were separated and the organic layer was washed successively with 500 ml of 1N hydrochloric acid, 500 ml of a 4% sodium hydroxide solution and once with brine, dried over anhydrous sodium sulfate and concentrated to give an oil as residue. The oil was subjected to vacuum distillation to give 34.4 g (22%) of clear oil (b.p. 147°–150° C. at 0.4 mm).

Analysis: Calculated for $C_7H_{12}ClNO_2$: C,47.33; H,6.81; N,7.89. Found: C,46.97; H,6.81; N,7.82.

PREPARATION 9

1-(Phenylmethyl)-4-piperidinecarboxylic acid ethyl ester hydrochloride

A mixture of 100 g (0.637 mole) of ethyl isonipecotate, 80.64 g (0.64 mole) of benzyl chloride and 67.84 g (0.64 mole) of sodium carbonate in 1 liter of absolute ethanol was refluxed for 8 hours and then was stirred at room temperature for 10 hours. The solvent was removed in vacuo, and the residue was partitioned between methylene chloride and dilute sodium hydroxide. The methylene chloride phase was dried over magnesium sulfate, and the solvent was removed in vacuo to give the free base of the title compound as a liquid. The free base was converted to the hydrochloride salt, and the salt was recrystallized from ethanol-ether to give 89.33 g (49.7%) of white, crystalline solid, m.p. 154°–155° C.

Analysis: Calculated for $C_{15}H_{22}NO_2Cl$: C,63.48; H,7.81; N,4.94. Found: C,63.07; H,7.82; N,4.91.

PREPARATION 10

α,α-bis-(4-Fluorophenyl)-1-(phenylmethyl)-4-piperidinemethanol

To magnesium turnings (6.08 g, 0.25 mole) and an iodine crystal in 600 ml of dry tetrahydrofuran (THF) (distilled from lithium aluminum hydride) and under an atmosphere of nitrogen was added dropwise a solution of p-bromofluorobenzene in 125 ml of THF. The temperature of the reaction mixture was kept below 10° C. by cooling in an ice-methanol bath. The mixture was stirred at room temperature for 1.5 hr. A solution of 1-(phenylmethyl)-4-piperidinecarboxylic acid ethyl ester (24.7 g, 0.10 mole) in THF was added, and the mixture was stirred at room temperature for 17 hr. The reaction mixture was poured into an icy, aqueous solution of ammonium chloride, and the resulting solution was extracted with methylene chloride. The solution was extracted with dilute sodium hydroxide and was dried (magnesium sulfate). The solvent was removed in vacuo to give an oil. This was crystallized from ether-hexane to give 19.87 g (51%) of title compound, m.p. 113°–115° C.

Analysis: Calculated for $C_{25}H_{25}NOF_2$: C,76.31; H,6.40; N,3.56. Found: C,76.24; H,6.38; N,3.50.

PREPARATION 11

α,α-Bis(p-fluorophenyl)-4-piperidinemethanol

A solution of 31.2 g (0.079 mole) of α,α-bis-(4-fluorophenyl)-1-(phenylmethyl)-4-piperidinemethanol in 400 ml of absolute ethanol was hydrogenated at 50 psi and 70° C. over 5% palladium-on-carbon over the weekend. The mixture was filtered and the filtrate was concentrated under reduced pressure to give a gum as residue. Methylene chloride was added to the residue and the gum crystallized. The mixture was diluted with petroleum ether and the solid was collected by filtration, washed with petroleum ether and dried to yield 22 g (99%) of white solid which was recrystallized from isopropyl ether and 2-propanol, m.p. 159.5°–160.5° C.

Analysis: Calculated for $C_{18}H_{19}F_2NO$: C,71.27; H,6.31; N,4.62. Found: C,70.93; H,6.71; N,4.38.

PREPARATION 12

α,α-Bis(4-methylphenyl)-1-(phenylmethyl)-4-piperidinemethanol

A Grignard solution was prepared by the addition of 102.6 g (0.6 mole) of 4-bromotoluene in 500 ml of dry tetrahydrofuran (THF) to a mixture of 12.5 g (0.5 mole) of magnesium chips in 250 ml of THF. After the addition was complete, the mixture was heated at reflux for 1 hr to complete formation. To this Grignard reagent at ambient temperature was added in a stream 42.9 g (0.173 mole) of 1-(phenylmethyl)-4-piperidinecarboxylic acid ethyl ester in 250 ml of dry THF. The solution was stirred at ambient temperature overnight and then poured into 2.5 liters of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water, and 250 ml of brine. The organic layer was dried over sodium sulfate and concentrated under reduced pressure to give a gum as residue. The gum gradually crystallized. The solid was triturated with petroleum ether (30°–60° C.), collected by filtration and dried to yield 63.6 g (95%) of white solid. An analytical sample, m.p. 115°–117° C., was prepared from 2-propanol.

Analysis: Calculated for $C_{27}H_{31}NO$: C,84.11; H,8.10; N,3.63. Found: C,84.23; H,8.13; N,3.66.

PREPARATION 13

α,α-Bis(4-methylphenyl)-4-piperidinemethanol

A solution of 38.5 g (0.1 mole) of α,α-bis(4-methylphenyl)-1-(phenylmethyl)-4-piperidinemethanol in 500 ml of absolute ethanol was hydrogenated at 50 psi and 60° C. over 5% palladium on carbon in a Parr apparatus for 3 days. The cooled mixture was filtered through Celite ® and the filtrate was concentrated under reduced pressure to give a glass as residue. The glass was crystallized from 2-propanol to yield 17.7 g (60%) of white solid, m.p. 150°–153° C.

Analysis: Calculated for $C_{20}H_{25}NO$: C,81.31; H,8.53; N,4.74. Found: C,81.18; H,8.62; N,4.72.

PREPARATION 14

α,α-Bis(4-methoxyphenyl)-1-(phenylmethyl)-4-piperidinemethanol oxalate hydrate methanolate [1:1:0.5:0.5]

A Grignard reagent was prepared by the addition of a solution of 112.2 g (0.6 mole) of 4-bromoanisole in 500 ml of dry tetrahydrofuran (THF) to a mixture of 12.5 g (0.5 mole) of magnesium chips in 250 ml of THF. After the addition was complete, the mixture was heated at reflux for 0.5 hr to complete formation. To this Grignard reagent at ambient temperature was added a solution of 42.8 g (0.173 mole) of 1-(phenylmethyl)-4-piperidinecarboxylic acid ethyl ester in 250 ml of THF in a stream. The mixture was stirred at ambient temperature overnight and then poured into 2.5 liters of a saturated ammonium chloride solution. The layers were separated and the aqueous layer was extracted twice with 375 ml portions of methylene chloride. The combined organic layers were washed successively with 500 ml of water, 750 ml of a 3% sodium hydroxide solution, 250 ml of water and 250 ml of brine. The organic layer was dried over sodium sulfate and concentrated under reduced pressure to give a gum as residue. The gum was dissolved in 2-propanol and converted to the oxalic acid salt. The solid was collected by filtration, washed with 2-propanol and ethyl ether, and dried to yield 84.8 g (97%) of white powder. An analytical sample, m.p. 128°–131° C. with decomposition (slow heating; rapid heating gives m.p. ~110° C.), was prepared from absolute ethanol.

Analysis: Calculated for $C_{29}H_{33}NO_7 \cdot 0.5H_2O \cdot 0.5C_2H_5OH$: C,66.74; H,6.91; N,2.60. Found: C,67.08; H,6.77; N,2.67.

PREPARATION 15

α,α-Bis(4-methoxyphenyl)-4-piperidinemethanol

A solution of 36.7 g (0.088 mole) of α,α-bis(4-methoxyphenyl)-1-(phenylmethyl)-4-piperidinemethanol in 500 ml of absolute ethanol was hydrogenated over palladium on carbon at 60° C. in a Parr apparatus over the weekend. The mixture was cooled, filtered through Celite ®, fresh catalyst added to the filtrate and the mixture hydrogenated. This process was repeated so that no starting material was present by mass spectral analysis. The filtrate was concentrated and the residue was partitioned between methylene chloride and a 5% sodium hydroxide solution. The organic layer was dried over sodium sulfate and concentrated to give a solid residue. The solid was recrystallized from 2-propanol to yield 8.6 g (30%) of white solid, m.p. 153°–155° C.

Analysis: Calculated for $C_{20}H_{25}NO_3$: C,73.37; H,7.70; N,4.28. Found: C,73.42; H,7.72; N,4.30.

PREPARATION 16

α,α-Diphenyl-1-(phenylmethyl)-4-piperidinemethanol

A Grignard solution was prepared by the addition of 94.2 g (0.6 mole) of bromobenzene in 250 ml of dry (freshly distilled from lithium aluminum hydride) tetrahydrofuran (THF) to a mixture of 12.5 g (0.5 mole) of magnesium chips in 500 ml of dry THF. After the addition was complete, the mixture was heated at reflux for 15 min to complete formation. To this Grignard reagent at ambient temperature was added a solution of 44.2 g (0.179 mole) of 1-(phenylmethyl)-4-piperidinecarboxilic acid ethyl ester in 250 ml of THF in a stream. The solution was stirred overnight at ambient temperature and then poured into 2.5 liters of a saturated ammonium chloride solution. The layers were separated and the aqueous layer was extracted once with 500 ml of methylene chloride and twice with 250 ml of methylene chloride. The combined organic layers were washed successively with 500 ml of water, 750 ml of a 3% sodium hydroxide solution, 250 ml of water and 250 ml of brine. The organic layer was dried over sodium sulfate and concentrated to give a gum as residue. The gum was dissolved in 500 ml of ethyl ether, treated with activated charcoal, filtered through Celite®, and then concentrated to give a gum as residue. The gum crystallized when triturated with petroleum ether (30°-60° C.). The solid was collected by filtration and dried to yield 49.0 g (77%) of white solid. An analytical sample, m.p. 89.5°-90.5° C. was prepared from 2-propanol.

Analysis: Calculated for $C_{25}H_{27}NO$: C,83.99; H,7.61; N,3.92. Found: C,84.09; H,7.63; N,3.97.

PREPARATION 17

α,α-Diphenyl-4-piperidinemethanol

A mixture of 35.8 g (0.1 mole) of α,α-diphenyl-1-(phenylmethyl)-4-piperidinemethanol and 5% palladium on carbon in 500 ml of absolute ethanol was hydrogenated at 60° C. in a Parr apparatus for 3 days. The mixture was filtered through Celite® and the filtrate was concentrated to give a solid residue. The solid was triturated with petroleum ether (30°-60° C.), collected by filtration and dried to give 26.7 g (quantitative) of white solid. An analytical sample, m.p. 160°-161° C. was prepared from 2-propanol-isopropyl ether.

Analysis: Calculated for $C_{18}H_{21}NO$: C,80.86; H,7.92; N,5.24. Found: C,80.98; H,7.96; N,5.30.

PREPARATION 18

4-[bis(4-Chlorophenyl)hydroxymethyl]-N,N-diethyl-1-piperidinecarboxamide

A Grignard solution was prepared by the treatment of a slurry of 8.5 g (0.35 mole) of magnesium chips in 200 ml of dry tetrahydrofuran (THF) with a solution of 72.8 g (0.38 mole) of 1-bromo-3-chlorobenzene in 400 ml of THF. After the addition was complete, the mixture was heated at reflux for 15 min to complete formation. To the Grignard solution at ambient temperature was added a solution of 38.4 g (0.15 mole) of 1-[(diethylamino)carbonyl]-4-piperidine carboxylic acid ethyl ester in 200 ml of THF in a stream. The solution was stirred at ambient temperature overnight and poured into 2.5 liters of a saturated ammonium chloride solution. The layers were separated and the aqueous layer was extracted once with 500 ml of methylene chloride and once with 250 ml of methylene chloride. The combined organic layers were filtered through Celite® and the filtrate was washed successively with 500 ml of water, 750 ml of a 4% sodium hydroxide solution, 250 ml of water and 250 ml of brine. The solution was dried over anhydrous sodium sulfate and concentrated under reduced pressure to give a gum which crystallized. The solid was triturated with petroleum ether (30°-60° C.), collected by filtration, and dried to yield 56.7 g (87,) of a white solid. An analytical sample, m.p. 172°-175° C. was prepared from 2-propanol.

Analysis: Calculated for $C_{23}H_{28}Cl_2N_2O_2$: C,63.54; H,6.48; N,6.43. Found: C,63.60; H,6.64; N,6.25.

PREPARATION 19

α,α-Bis(4-chlorophenyl)-4-piperidinemethanol

To a slurry of 8.5 g (0.225 mole) of lithium aluminum hydride in 400 ml of anhydrous tetrahydrofuran (THF) was added a solution of 39.2 g (0.09 mole) of 4-[bis(4-chlorophenyl)hydroxymethyl]-N,N-diethyl-1-piperidinecarboxamide in 400 ml of THF in a stream over a 15 min period. The mixture was heated at reflux for 24 hr, cooled, and treated successively with 8.5 ml of water, 25 ml of a 3N sodium hydroxide solution and 8.5 ml of water. The mixture was stirred for 0.5 hr and then filtered. The filtrate was concentrated under reduced pressure to give a gum which crystallized. The solid was triturated with petroleum ether (30°-60° C.), collected by filtration and recrystallized from benzene to yield 10.5 g (35%) of white solid. An analytical sample, m.p. 184°-188° C. was prepared from 2-propanol.

Analysis: Calculated for $C_{16}H_{19}Cl_2NO$: C,64.30; H,5.70; N,4.17. Found: C,64.59; H,5.79; N,4.16.

PREPARATION 20

1Acetyl-4-(p-fluorobenzoyl)piperidine

The title compound was prepared as disclosed in U.S. Pat. No. 3,576,810 as follows: A mixture of 93 g (0.7 mole) of aluminum chloride in 150 ml of fluorobenzene was stirred while 70 g (0.37 mole) of 1-acetylisonipecotic acid chloride was added in small portions. After the addition was complete, the mixture was refluxed for one hour. The mixture was poured onto ice and the two resulting layers were separated. The aqueous layer was extracted twice with chloroform and the chloroform extracts were added to the fluorobenzene which was separated previously. The organic solution was dried over anhydrous sodium sulfate and filtered. The filtrate was concentrated and 73.7 g (80%) of 1-acetyl-4-(p-fluorobenzoyl)-piperidine was obtained as a crystalline residue. Recrystallization from ligroin-isopropyl ether gave a white crystalline product melting at 75°-78° C.

Analysis: Calculated for $C_{14}H_{16}FNO_2$: C,67.45; H,6.47; N,5.62. Found: C,67.26; H,6.50; N,5.54.

PREPARATION 21

1-Acetyl-α-(4-fluorophenyl)-α-phenyl-4-piperidinemethanol

A solution (667 ml, 2 mole) of phenylmagnesium bromide (3M in ethyl ether) was diluted with 2 liters of anhydrous ethyl ether, cooled to 0°-10° C. and treated with a solution of 148 g (0.6 mole) of 1-acetyl-4-(p-fluorobenzoyl)-piperidine in 1.5 liter of anhydrous tetrahydrofuran dropwise over a 1.5 hr period. The mixture was stirred at ambient temperature overnight and then poured into a solution of 107 g (2 mole) of ammonium chloride in 2 liters of cold water. The mixture was extracted thrice with 1 liter portions of benzene. The combined extracts were washed with water, dried over magnesium sulfate, and concentrated to give a semi-solid as residue. The semi-solid was triturated with isopropyl ether and the mass cyrstallized. The solid was collected by filtration and dried to yield 87.8 g (45%) of white solid. An analytical sample, m.p. 173°-175° C., was prepared from 2-propanol.

Analysis: Calculated for $C_{20}H_{22}FNO$ C,73.37; H,6.77; N,4.28. Found: C,73.20; H,6.93; N,4.22.

PREPARATION 22

α-(4-Fluorophenyl)-α-phenyl-4-piperidinemethanol

A mixture of 16.3 g (0.05 mole) of 1-acetyl-α-(4-fluorophenyl)-α-phenyl-4-piperidinemethanol and 5.6 g (0.1 mole) of potassium hydroxide in 150 ml of 95% ethanol and 20 ml of water was heated at reflux for 18 hr. The mixture was poured into 1.5 liter of ice water and a solid precipitated. The solid was collected by filtration and dried. The gummy solid was dissolved in ethyl ethyl ether, the solution was filtered, and the filtrate slowly evaporated to 50 ml volume. The resulting solid was collected by filtration and recrystallized from 2-propanol-isopropyl ether to yield 3.5 g (25%) of white solid, m.p. 144.5°–146° C.

Analysis: Calculated for $C_{18}H_{20}FNO$: C,75.76; H,7.06; N,4.91. Found: C,75.91; H,7.20; N,4.93.

PREPARATION 23

4-[(3-Chloro)propyl]-3-methyl-2-oxazolidinone

A cold (ice bath) solution of 4.0 g (0.041 mole) of phosgene dissolved in 50 ml of methylene chloride was treated dropwise with a solution of 4.7 g (0.041 mole) of 2-hydroxymethyl-1-methylpyrrolidine in 15 ml of methylene chloride at such a rate that the temperature did not exceed 10° C. After addition was complete, the solution was stirred in the cold for 1 hr and then treated dropwise with 4.0 g (0.041 mole) of triethylamine at such a rate that the temperature did not exceed 25° C. The mixture was stirred at ambient temperature for 3 hr and then treated with 50 ml of 1N hydrochloric acid. The layers were separated and the organic layer was washed successively with 50 ml of 1N hydrochloric acid, 50 ml of 4% sodium hydroxide, and 50 ml of brine. The organic layer was dried over sodium sulfate and concentrated to give 2.5 g of oil as residue. This oil was purified by column chromatography on 50 g of silica gel eluted with benzene. Fractions containing the desired product were combined and concentrated to give 1.8 g (25%) of product as an oil.

PREPARATION 24

α-(4-Fluorophenyl)-α-(4-piperidinyl)-2-pyridinemethanol

To a stirred solution of 36.3 g (0.23 mol) of 2-bromopyridine in 500 mL of anhydrous tetrahydrofuran (THF) at −65° C. was added 88 mL (0.22 mol) of a commercial solution of 2.5M n-butyllithium in hexane at such a rate that the temperature did not exceed −60° C. The dark solution was stirred at −65° C. for 1 hr and then treated dropwise with a solution of 24.9 g (0.1 mol) of 1-acetyl-4-(p-fluorobenzoyl)piperidine (See Preparation 1 of U.S. Pat. No. 4,151,285, col. 4, lines 10–30, herein incorporated by reference) in 250 mL of THF at such a rate that the temperature did not exceed −60° C. The mixture was stirred for 1 hr at −65° C. and overnight at ambient temperature. The dark mixture was poured into 2 liters of a saturated ammonium chloride solution. The layers were separated and the aqueous layer was extracted once with a 500-mL portion of methylene chloride. The combined organic layers were washed successively with 500 mL of water, 500 mL of a 4% sodium hydroxide solution, 250 mL of water, and 250 mL brine.

All of the combined aqueous layers were combined and allowed to stand in a filter flask for several weeks. As the soluble organic solvents in the aqueous solution evaporated, a solid precipitated. The aqueous solution was decanted and the solid was slurried with water, collected by filtration, and dried. The solid was recrystallized from absolute ethanol-pyridine to yield 4.5 g (14%) of the title compound as an off-white solid, mp 228°–230° C. (dec).

Analysis: Calculated or $C_{17}H_{19}FN_2O$: C, 71.31; H, 6.69; N, 9.78. Found: C, 71.43; H, 6.54; N, 9.52.

PREPARATION 25

α-(4-piperidinyl)-α-(2-pyridinyl)-2-pyridinemethanol

To a stirred solution of 71.1 g (0.45 mol) of 2-bromopyridine in 750 mL of anhydrous tetrahydrofuran (THF) at −65° C. is added 176 mL (0.44 mol) of a commercial solution of 2.5-M n-butyllithium in hexane at such a rate that the temperature does not exceed −60° C. The dark solution is stirred at −65° C. for 1 hr and is then treated dropwise with a solution of 39.8 g (0.2 mol) of ethyl-1-acetylpiperidine-4-carboxylate [G. R. Clemo and E. Hoggarth, J. Chem. Soc.: London 41–47 (1941)] in 500 mL of THF at such a rate that the temperature does not exceed −60° C. The mixture is stirred for 1 hr at −65° C. and allowed to stand at ambient temperature overnight. The dark mixture is poured into 3 liters of a saturated ammonium chloride solution and the layers are evaporated. The aqueous layer is extracted once with 1 liter of methylene chloride. The combined organic layers are washed successively with 1 liter of water, 1 liter of 4% sodium hydroxide solution, 500 mL of water, and 500 mL of brine.

The organic layer is concentrated and the residue is dissolved in 1 liter of ethanol. The solution is treated with 28 g (0.5 mol) of potassium hydroxide dissolved in 100 mL of water and the mixture is heated at reflux for 6 hr. The mixture is concentrated and the residue is partitioned between methylene chloride and water. The organic layer is washed with water and brine, dried (sodium sulfate), and concentrated to yield the title compound.

EXAMPLE 1

5-[2-[4[Bis(4-fluorophenyl)hydroxymethyl]-1-piperidinyl]ethyl]-3-methyl-2-oxazolidinone oxalate [1:1]

A mixture of 3.0 g (0.01 mole) of α,α-bis(p-fluorophenyl)-4-piperidinemethanol, 1.6 g (0.01 mole) of 5-(2-chloroethyl)-3-methyl-2-oxazolidinone, 5.3 g (0.085 mole) of anhydrous sodium carbonate and 0.3 g of potassium iodide in 100 ml of 1-butanol was heated at reflux for 20 hr. The mixture was concentrated under reduced pressure and the residue was partitioned between water and benzene. The benzene layer was washed with water and brine, dried over anhydrous sodium sulfate and concentrated under reduced pressure to give a gum as residue. The gum was converted to the oxalic acid salt, recrystallizing from absolute ethanol to give 3.7 g (71%) of white powder, m.p. 124°–134° C. with decomposition.

Analysis: Calculated for $C_{26}H_{30}F_2N_2O_7$: C,59.99; H,5.81; N,5.38. Found: C,59.59; H,5.83; N,5.36.

EXAMPLE 2

5-[2-[Bis(4-fluorophenyl)hydroxymethyl]-1-piperidinyl]ethyl]-3-methyl-2-oxazolidinone fumarate [1:1]

Utilizing the procedure of Example 1, a mixture of 9.1 g (0.03 mole) of α,α-bis(p-fluorophenyl)-4-piperidinemethanol, 4.9 g (0.03 mole of 5-(2-chloroethyl)-3-methyl-2-oxazolidinone, 10.6 g (0.1 mole) of anhydrous sodium carbonate and 0.6 g of potassium iodide in 200 ml of butanol were reacted and the mixture concentrated to give a gum. The fumaric acid salt was prepared, recrystallizing from absolute ethanol, to give 10.0 g (61%) of white solid, m.p. 160.5°–162.5° C. with decomposition.

EXAMPLE 3

5-[2-[4-Bis(4-methylphenyl)hydroxymethyl]-1-piperidinyl]ethyl-3-methyl-2-oxazolidinone oxalate hydrate [1:1:0.5]

This compound was prepared according to the procedure of Example 1. A mixture of 4.4 g (0.015 mole) of α,α-bis-(4-methylphenyl)-4-piperidinemethanol, 2.5 g (0.015 mole) of 5-(2-chloroethyl-3-methyl-2-oxazolidinone, 5.3 g (0.05 mole) of anhydrous sodium carbonate and 0.4 g of potassium iodide in 100 ml of 1-butanol gave a gum as residue. The gum was dissolved in ethyl ether, treated with activated charcoal, filtered through Celite®, and the filtrate concentrated under reduced pressure to give a glass as residue. The glass was converted to the oxalic acid salt and the solid was recrystallized from 95% ethanol to yield 4.8 g (62%) of white solid, m.p. 146°–159° C., with decomposition.

Analysis: Calculated for $C_{28}H_{36}N_2O_7 \cdot 0.5H_2O$: C,64.48; H,7.15; N,5.37. Found: C,64.92; H,7.11; N,5.39.

EXAMPLE 4

S-(−)-5-[2-[4-[Bis(4-fluorophenyl)hydroxymethyl]-1-piperidinyl]ethyl]-3-methyl-2-oxazolidinone fumarate [1:1]

This compound was prepared according to the procedure of Example 1. A mixture of 9.1 g (0.03 mole) of α,α-bis-(p-fluorophenyl)-4-piperidinemethanol, 4.9 g (0.03 mole) of S-(−)-5-(2-chloroethyl)-3-methyl-2-oxazolidinone, 10.6 g (0.10 mole) of anhydrous sodium carbonate and 0.9 g of potassium iodide in 200 ml of 1-butanol gave a gum as residue. The gum was converted to the fumaric acid salt and this solid was recrystallized from absolute ethanol to yield 11.0 g (67%) of white solid, m.p. 154°–157° C., with decomposition; $[\alpha]_D^{25}$ −16.1° C. (methanol).

Analysis: Calculated for $C_{28}H_{32}F_2N_2O_7$: C,61.53; H,5.90; N,5.13. Found: C,61.30; H,5.93; N,5.14.

EXAMPLE 5

R-(+)-5-[2-[4-[Bis(4-fluorophenyl)hydroxymethyl]-1-piperidinyl]ethyl-3-methyl-2-oxazolidinone fumarate [1:1]

This compound was prepared according to the procedure of Example 1. A mixture of 9.1 g (0.03 mole) of α,α-bis-(p-fluorophenyl)-4-piperidinemethanol, 4.9 g (0.03 mole) of R-(+)-5-(2-chloroethyl)-3-methyl-2-oxazolidinone, 10.6 g (0.10 mole) of anhydrous sodium carbonate and 0.5 g of potassium iodide in 200 ml of 1-butanol gave a gum as residue. The gum was converted to the fumaric acid salt and this solid was recrystallized from absolute ethanol to yield 9.0 g (55%) of white solid, m.p. 153°–156° C., with decomposition; $[\alpha]_D^{25}$ +19.5° C. (methanol).

Analysis: Calculated for $C_{29}H_{31}F_2NO_5$: C,61.53; H,5.90; N,5.13. Found: C,61.32; H,5.85; N,5.12.

EXAMPLE 6

5-[2-[4-[Bis(4-methoxyphenyl)hydroxymethyl]-1-piperidinyl]ethyl]-3-methyl-2-oxazolidinone This compound was prepared according to the procedure of Example 1. A mixture of 3.2 g (0.01 mole) of α,α-bis-(4-methoxyphenyl)-4-piperidinemethanol, 1.6 g (0.01 mole) of 5-(2-chloroethyl)-3-methyl-2-oxazolidinone, 3.7 g (0.035 mole) of anhydrous sodium carbonate and 0.4 g of potassium iodide in 100 ml of 1-butanol gave 3.9 g (87%) of off-white solid, m.p. 145°–147° C. (2-propanol).

Analysis: Calculated for $C_{26}H_{34}N_2O_5$: C,68.70; H,7.54; N,6.16. Found: C,68.45; H,7.60; N,6.11.

EXAMPLE 7

5-[2-[4-[Bis(4-fluorophenyl)hydroxymethyl]-1-piperidinyl]ethyl]-3-phenyl-2-oxazolidinone hydrochloride [1:1]

This compound was prepared according to the procedure of Example 1. A mixture of 4.6 g (0.015 mole) of α,α-bis-(p-fluorophenyl)-4-piperidinemethanol, 3.4 g (0.015 mole) of 5-(2-chloroethyl)-3-phenyl-2oxazolidinone, 5.3 g (0.05 mole) of anhydrous sodium carbonate and 0.4 g of potassium iodide in 100 ml of 1-butanol gave a gum as residue. The gum was converted to the hydrochloride and the solid was recrystallized from absolute ethanol to yield 6.3 g (30%) of white solid, m.p. 148°–156° C., with decomposition.

Analysis: Calculated for $C_{29}H_{31}ClF_2N_2O_3$: C,65.84; H,5.91; N,5.30. Found: C,65.40; H,5.98; N,5.27.

EXAMPLE 8

5-[3-[4-[Bis(4-fluorophenyl)hydroxymethyl]-1-piperidinyl]propyl]-3-methyl-2-oxazolidinone oxalate [1:1]

This compound was prepared according to the procedure of Example 1. A mixture of 4.6 g (0.015 mole) of α,α-bis-(p-fluorophenyl)-4-piperidinemethanol, 2.7 g (0.015 mole) of 5-(3-chloropropyl)-3-methyl-2-oxazolidinone, 5.3 g (0.05 mole) of anhydrous sodium carbonate and 0.4 g of potassium iodide in 100 ml of 1-butanol gave a gum as residue. The gum was converted to the oxalic acid salt and the solid was recrystallized from absolute ethanol to yield 4.5 g (54%) of white solid, m.p. 150°–153° C., with decomposition.

Analysis: Calculated for $C_{27}H_{32}F_2N_2O_7 \cdot H_2O$: C,58.67; H,6.20; N,5.07. Found: C,58.77; H,5.89; N,4.98.

EXAMPLE 9

6-[2-[4-[Bis(4-fluorophenyl)hydroxymethyl]-1-piperidinyl]ethyl]-3-methyl-tetrahydro-2H-1,3-oxazin-2-one oxalate [1:1]

This compound was prepared according to the procedure of Example 1. A mixture of 4.6 g (0.015 mole) of α,α-bis-(p-fluorophenyl)-4-piperidinemethanol, 2.7 g (0.015 mole) of 6-(2-chloroethyl)tetrahydro-3-methyl-2H-1,3-oxazin-2-one, 5.3 g (0.05 mole) of anhydrous sodium carbonate and 0.4 g of potassium iodide in 100 ml of 1-butanol gave a glass as residue. The glass was converted to the oxalate and the solid was recrystallized from absolute ethanol to yield 4.9 g (61%) of white solid, m.p. 193°–194° C., with decomposition.

Analysis: Calculated for $C_{27}H_{32}F_2N_2O_7$: C,60.67; H,6.03; N,5.24. Found: C,60.45; H,6.06; N,5.21.

EXAMPLE 10

5[[4-[Bis(4-fluorophenyl)hydroxymethyl]-1-piperidinyl]methyl]-3-methyl-2-oxazolidinone This compound was prepared according to the procedure of Example 1. A mixture of 4.6 g (0.015 mole) of α,α-bis-(p-fluorophenyl)-4-piperidinemethanol, 2.2 g (0.015 mole) of 5-(chloromethyl)-3-methyl-2-oxazolidinone, 5.3 g (0.05 mole) of anhydrous sodium carbonate and 0.4 g of potassium iodide in 100 ml of 1-butanol gave a gum as residue. The gum was purified by column chromatography on 50 g of Florisil ®. Fractions eluted with 5–20% acetone in benzene were combined and concentrated to give a solid residue. The solid was recrystallized from isopropyl ether-2-propanol to yield 1.5 g (24%) of white solid, m.p. 147°–148° C.

Analysis: Calculated for $C_{23}H_{26}F_2N_2O_3$: C,66.33; H,6.29; N,6.73. Found: C,66.32; H,6.35; N,6.68.

EXAMPLE 11

5-[2-[4-[Bis(4-fluorophenyl)hydroxymethyl]-1-piperidinyl]ethyl]-3-phenylmethyl-2-oxazolidinone oxalate [1:1]

This compound was prepared according to the procedure of Example 1. A mixture of 9.1 g (0.03 mole) of α,α-bis-(p-fluorophenyl)-4-piperidinemethanol, 7.2 g (0.03 mole) of 5-(2-chloroethyl)-3-benzyl-2-oxazolidinone, 10.6 g (0.1 mole) of anhydrous sodium carbonate and 0.4 g of potassium iodide in 175 ml of 1-butanol gave a gum as residue. The gum was converted to the oxalate salt and the solid was recrystallized from 2-methoxyethanol-water to yield 13.5 g (75%) of white solid, m.p. 234°–235° C., with decomposition.

Analysis: Calculated for $C_{32}H_{34}F_2N_2O_7$: C,64.42; H,5.74; N,4.70. Found: C,64.33; H,5.75; N,4.69.

EXAMPLE 12

5-[2-[4-[Bis(4-fluorophenyl)hydroxymethyl]-1-piperidinyl]ethyl]-3-phenyl-2-oxazolidinone hydrochloride hydrate [1:1:0.5]

This compound was prepared according to the procedure of Example 1. A mixture of 4.5 g (0.015 mole) of α,α-bis-(p-fluorophenyl)-4-piperidinemethanol, 3.5 g (0.015 mole) of 5-(2-chloroethyl)-3-phenyl-2-oxazolidinone, 5.3 g (0.05 mole) of anhydrous sodium carbonate and 0.4 g of potassium iodide in 100 ml of 1-butanol gave a brown gloss as residue. The glass was converted to the hydrochloride and the solid was recrystallized from 95% ethanol to yield 6.3 g (79%) of white solid, m.p. 180°–183° C. with decomposition.

Analysis: Calculated for $C_{29}H_{37}ClF_2N_2O_3 \cdot 0.5H_2O$: C,64.02; H,7.04; N,5.15. Found: C,63.90; H,7.39; N,4.92.

EXAMPLE 13

5-[2-[4-[Bis(4-fluorophenyl)hydroxymethyl]-1-piperidinyl]ethyl]-3-ethyl-2-oxazolidinone oxalate hydrate [1:1:0.5]

This compound was prepared according to the procedure of Example 1. A mixture of 4.5 g (0.015 mole) of α,α-bis-(p-fluorophenyl)-4-piperidinemethanol, 2.7 g (0.015 mole) of 5-(2-chloroethyl-3-ethyl-2-oxazolidinone, 5.3 g (0.05 mole) of anhydrous sodium carbonate and 0.4 g of potassium iodide in 100 ml of 1-butanol gave a glass as residue. The glass was converted to the oxalic acid salt and the solid was recrystallized from absolute ethanol to yield 5.1 g (64%) of white solid, m.p. 130°–132° C.

Analysis: Calculated for $C_{27}H_{32}F_2N_2O_7 \cdot 0.5H_2O$: C,59.66; H,6.12; N,5.15. Found C,59.92; H,5.97; N,5.21.

EXAMPLE 14

5-[2-[4-[Bis(4-fluorophenyl)hydroxymethyl]-1-piperidinyl]ethyl]-3-(1-methylethyl)-2-oxazolidinone fumarate [1:1]

This compound was prepared according to the procedure of Example 1. A mixture of 4.6 g (0.015 mole) of α,α(p-fluorophenyl)-4-piperidinemethanol, 2.9 g (0.015 mole) of 5-(2-chloroethyl)-3-(1-methylethyl)-2-oxazolidinone, 5.3 g (0.05 mole) of anhydrous sodium carbonate and 0.4 g of potassium iodide in 100 ml of 1-butanol gave a gum as residue. The gum was converted to the fumaric acid salt and the solid was recrystallized from absolute ethanol to yield 3.2 g (37%) of white solid, m.p. 219°–221° C., with decomposition.

Analysis: Calculated for $C_{30}H_{36}F_2N_2O_7$: C,62.71; H,6.31; N,4.87. Found: C,62.75; H,6.33; N,4.90.

EXAMPLE 15

5-[2-[4-[Bis(phenyl)hydroxymethyl]-1-piperidinyl]ethyl]-3-methyl-2-oxazolidinone oxalate Following the procedure of Example 1, α,α-diphenyl-4-piperidinemethanol and 5-(2-chloroethyl)-3-methyl-2-oxazolidinone are reacted and the product thereof is reacted with oxalic acid to give the title compound.

EXAMPLE 16

5-[2-[4-[Bis(4-chlorophenyl)hydroxymethyl]-1-piperidinyl]ethyl]-3-methyl-2-oxazolidinone oxalate Following the procedure of Example 1, α,α-bis(4-chlorophenyl)-4-piperidinemethanol and 5-(2-chloroethyl)-3-methyl-2-oxazolidinone are reacted and the product thereof is reacted with oxalic acid to give the title compound.

EXAMPLE 17

5-[2-[4-[α-(4-Phenyl)-α-phenyl-hydroxymethyl]-1-piperidinyl]ethyl]-3-methyl-2-oxazolidinone oxalate Following the procedure of Example 1, α-(4-fluorophenyl)-α-phenyl-4-piperidinemethanol and 5-(2-chloroethyl)-3-methyl-2-oxazolidinone are reacted and the product thereof is reacted with oxalic acid to give the title product.

EXAMPLE 18

Following the procedure of Example 1 and substituting the following for 5-(2-chloroethyl)-3-methyl-2-oxazolidinone:
5-(2-chloroethyl)-3,4-dimethyl-2-oxazolidinone,
5-(2-chloroethyl)-3-(1-butyl)-2-oxazolidinone,
5-(1-methyl-2-chloroethyl)-3-methyl-2-oxazolidinone,
5-(4-chlorobutyl)-3-methyl-2-oxazolidinone,
5-(2-chloroethyl)-3-(4-methoxyphenyl)-2-oxazolidinone,
5-(2-chloroethyl)-3-(4-methylphenyl)-2-oxazolidinone,
5-(2-chloroethyl)-3-(3-chlorophenyl)-2-oxazolidinone, and,
3-benzyl-5-chloromethyl-2-oxazolidinone,
there are obtained:
(a)  5-[2-[4-[bis(4-fluorophenyl)hydroxymethyl]-1-piperidinyl]ethyl]-3,4-dimethyl-2-oxazolidinone oxalate,
(b)  5-[2-[4-[bis(4-fluorophenyl)hydroxymethyl]-1-piperidinyl]ethyl]-3-(1-butyl)-2-oxazolidinone oxalate,
(c)  5-[2-[4-[bis(4-fluorophenyl)hydroxymethyl]-1-piperidinyl]-(1-methylethyl)-3-methyl-2-oxazolidinone oxalate,
(d)  5-[4-[4-[bis(4-fluorophenyl)hydroxymethyl]-1-piperidinyl]butyl]-3-methyl-2-oxazolidinone oxalate,
(e)  5-[2-[4-[bis(4-fluorophenyl)hydroxymethyl]-1-piperidinyl]ethyl]-3-(4-methoxyphenyl)-2-oxazolidinone oxalate, (f) 5-[2-[4-[bis(4-fluorophenyl)hydroxymethyl]-1-piperidinyl]ethyl]-3-(4-methylphenyl)-2-oxazolidinone oxalate, (g) 5-[2-[4-[bis(4-fluorophenyl)hydroxymethyl]-1-piperidinyl]ethyl]-3-(3-chlorophenyl)-2-oxazolidinone oxalate, and (h) 5-[2-[4-[bis(4-fluorophenyl)hydroxymethyl]-1-piperidinyl]methyl]-3-(phenylmethyl)-2-oxazolidinone.

EXAMPLE 19

4-[3-[4-[Bis(4-fluorophenyl)hydroxymethyl]-1-piperidinyl]propyl]-3-methyl-2-oxazolidinone oxalate Following the procedure of Example 1, $\alpha,\alpha$-bis(p-fluorophenyl)-4-piperidinemethanol and 4-[(3-chloro)propyl]-3-methyl-2-oxazolidinone are reacted and the product thereof is reacted with oxalic acid to give the title compound.

EXAMPLE 20

7-[2-[4-[Bis(4-fluorophenyl)hydroxymethyl]-1-piperidinyl]ethyl]-3-methyl-hexahydro-2H-1,3-oxazepin-2-one oxalate Following the procedure of Example 1, $\alpha,\alpha$-bis(p-fluorophenyl)-4-piperidinemethanol and 7-(2-chloroethyl)hexahydro-3-methyl-2H-1,3-oxazepin-2-one are reacted and the product thereof is reacted with oxalic acid to give the title compound.

EXAMPLE 21

8-[2-[4-[Bis(4-fluorophenyl)hydroxymethyl]-1-piperidinyl]ethyl]-3-methyl-octahydro-2H-1,3-oxazocin-2-one oxalate Following the procedure of Example 1, $\alpha,\alpha$-bis-(p-fluorophenyl)-4-piperidinemethanol and 8-(2-chloroethyl)octahydro-3-methyl-2H-1,3-oxazocin-2-one are reacted and the product thereof is reacted with oxalic acid to give the title compound.

EXAMPLE 22

5-[2-[4-(4-fluorophenyl)(2-pyridinyl)hydroxymethyl]-1-piperidinyl]ethyl]-3-methyl-2-oxazolidinone A mixture of 2.9 g (0.01 mol) of $\alpha$-(4-fluorophenyl)-$\alpha$-(4-piperidinyl)-2-pyridinemethanol, 1.6 g (0.01 mol) of 5-(2-chloroethyl)-3-methyl-2-oxazolidinone, 3.7 g (0.035 mol) of anhydrous sodium carbonate and 0.1 g of potassium iodide in 100 mL of 1-butanol is heated at reflux for 16 hr. The mixture is concentrated and the residue is partitioned between benzene and water. The organic layer is washed with water and brine, dried over sodium sulfate, filtered, and concentrated to give the title compound.

EXAMPLE 23

5-[2-[4-[bis(2-pyridinyl)hydroxymethyl]-1-piperidinyl]ethyl]-3-methyl-2-oxazolidinone A mixture of 2.69 g (0.01 mol) of $\alpha$-(4-piperidinyl)-$\alpha$-(2-pyridinyl)-2-pyridinemethanol, 1.6 g (0.01 mol) of 5-(2-chloroethyl)-3-methyl-2-oxazolidinone, 3.7 g (0.035 mol) of anhydrous sodium carbonate and 0.1 g of potassium iodide in 100 mL of 1-butanol is heated at reflux for 16 hr. The mixture is concentrated and the residue is partitioned between benzene and water. The organic layer is washed with water and brine, dried over sodium sulfate, filtered and concentrated to give the title compound.

Pharmacology Methods Antiallergy Screening Method-Rats

As stated above, the primary screening method used to demonstrate antiallergy properties of the compounds of Formula I is a modification of the procedure of R. R. Martel and J. Klicius, International Archives Allergy Appl. Immunology, Vol. 54, pp 205–209 (1977) which measures the effect of oral administration of the compound on the volume of a rat paw which was previously injected with anti-egg albumin serum following egg albumin challenge. The procedure is as follows: Fed rats are injected in the right hind paw with 0.2 ml of rat anti-egg albumin serum at a dilution previously shown to produce significant edema upon antigen challenge. The animals are then fasted, but allowed water ad libitum. The next day the rats are randomized into groups of 6 by means of tables generated by the IBM scrambler. Random number tables are used to determine the groups receiving the control, reference and test articles. On the test day, the right foot volume of each rat is determined plethysmographically using the hairline as the reference point. Volume of this foot is measured with a mercury filled tube that is connected to a P23A Statham ® pressure transducer that in turn is connected to a linear Cole Parmer ® recorder (Model No. 255). The instrument is adjusted so that a pen deflection of 50 mm is equivalent to 1 ml volume. Separately, the reference and test compounds and control articles are dissolved or suspended in 0.5% Tween 80 in distilled water. Sonification is used to facilitate dissolution or reduce particle size. The animals are dosed orally (10 ml/kg) at 1 hr prior to the intravenous injection of the antigen, 2 mg of egg albumin in 0.2 ml of sterile saline. Thirty minutes later the right foot volume is measured again and edema is determined by difference. Results are expressed as the average foot edema (ml) $\pm$S.D. A significant decrease ($p<0.05$) in the edema of the treated group from that of the control group is considered as indicative of antiallergic activity. The results are acceptable only if the group receiving the reference article shows a significant decrease in foot edema. The foot volume for each animal is measured twice, once prior to dosing and again 30 min following the intravenous administration of antigen. Data is analyzed with the Dunnett's t-test that compares several treated groups with a control group. Differences between groups are determined by the studentized Range Test. Regression analysis may be used to determine relative potency.

Guinea Pig Anaphylaxis Method

The method used to test antiallergy effectiveness of the compounds in guinea pigs as compared to other drugs is as follows:

Guinea pigs are first sensitized to egg albumin (EA, Sigma Chemical Co., St. Louis, Missouri), at least 20 days prior to aerosol challenge by receiving 0.5 ml of EA-Al(OH)$_3$ conjugate (33 µg EA/ml) intramuscularly in each hind leg.

On the test day, fasted, sensitized guinea pigs are divided into a control group (8 animals per group) and test groups of four animals per group by using random number tables generated by an IBM scrambler. The reference; e.g., theophylline or test drug (Formula I cpd.) dissolved or suspended in 0.5% Tween 80 in distilled water or the control article (0.5% Tween 80 in distilled water) are administered orally in a volume of liquid at 10 ml/kg. Either 1, 5, or 24 hours following the oral administration of the test drug, reference drug, or control article, each animal is placed in an aerosolization chamber. EA (10 mg/ml) aerosolized at a rate of 10 liters of air/min is delivered into the chamber for a maximum of 5 minutes. The anaphylactic response consists of coughing, dyspnea, reeling, collapse and death. Upon collapsing, the animals are removed from the chamber. Animals are considered protected if they do not collapse within 5 min of exposure to the aerosolized antigen. The number of animals that collapse in each group is recorded. $ED_{50}$ for collapse is calculated by the method of Litchfield and Wilcoxon (1949), J. PHARMACOL. EXP. THERAP. 95, 99–113 for evaluation of dose-effect experiments.

Comparisons of $ED_{50}$s from different experimental trials and determinations of relative potency are determined by the Litchfield and Wilcoson method, ibid. The following conditions must be met before an experiment is acceptable:

(1) Control group shows collapse in ⅞ or 8/8 animals, and
(2) Theophylline reference group shows protection in ¾ or 4/4 animals treated 1 hr or 5 hr prior to antigen exposure.

Screening Procedure for Antihistamine Activity

The compounds of the present invention exhibit antihistamine activity in guinea pigs. The method of testing is a modification of the procedure of Tozzi et al (Agents and Actions, Vol. 4/4, 264–270, 1974) as follows: Guinea pigs are fasted 18–24 hrs in individual cages. Water is available ad libitum. On the test day, animals in groups of 3 are injected intraperitoneally with 30 mg/kg of the test compound prepared in an appropriate vehicle. Thirty minutes later histamine at a dosage level of 1.2 mg/kg ($=2\times$ the $LD_{99}$) is injected into a marginal ear vein. Survival of the guinea pigs for 24 hrs is positive evidence of antihistaminic activity. If the vehicle used for the test compound is other than water, its effect is established by testing an equal amount as a control. The dose protecting 50% of the animals ($PD_{50}$) from death may be established from dose-response curves.

Pharmaceutical Compositions and Administration

Compositions for administration to living animals are comprised of at least one of the compounds of Formula I according to the antiallergy method of the invention in association with a pharmaceutical carrier or excipient. Effective quantities of the compounds may be administered in any one of various ways; for example, orally as in elixirs, capsules, tablets or coated tablets, parenterally in the form of sterile solutions, suspensions, and in some cases intravenously in the form of sterile solutions, intranasally and to the throat or bronchial region in the form of drops, gargles, sprays, aerosols and powders, etc. or cutaneously as topical ointments, solutions, powders, etc. Suitable tableting excipients include lactose, potato and maize starches, talc, gelatin, stearic and silica acids, magnesium stearate and polyvinyl pyrrolidone.

For parenteral administration, the carrier or excipient can be comprised of a sterile parenterally acceptable liquid; e.g., water or arachis oil contained in ampoules.

Advantageously, the compositions are formulated as dosage units, each unit being adapted to supply a fixed dose of active ingredients. Tablets, coated tablets, capsules ampoules, sprays and suppositories are examples of preferred dosage forms. It is only necessary that the active ingredient constitute an effective amount such that a suitable effective dosage will be consistent with the dosage form employed, in multiples if necessary. The exact individual dosages, as well as daily dosages, will of course be determined according to standard medical principles under the direction of a physician or veterinarian. Generally, the pharmacology tests on guinea pigs in comparison to certain other antiallergy drugs suggest an effective dose for an adult will be in the range of 1.0 to 20 mg for the more active compounds with a daily dosage amounting to about 4 to 160 mg/day.

Based on the animal data, unit dosages containing an amount of compound equivalent to about 0.02 to 0.2 mg of active drug per kilogram of body weight are contemplated. Daily dosages of about 0.10 to 2.0 mg/kg of body weight are contemplated for humans and obviously several small dosage forms may be administered at one time. However, the amount of the active compounds administered need not be limited by these contemplations due to uncertainty in transposing animal data to human treatment.

Oral dosages projected for use as antihistamines for an adult human are of the order 10–120 mg/day divided into 2 or 3 doses. Thus, for example, one or two capsules each containing 10–40 mg active agent of Formula I could be administered 2-3 times daily for temporary relief of cough due to minor throat and bronchial irritation which may occur with the common cold or with inhaled irritants.

Examples of compositions within the preferred ranges given are as follows:

| | Capsules | |
|---|---|---|
| | Ingredients | Per Cap. |
| 1. | Active ingredient | 10.0 mg |
| 2. | Lactose | 146.0 mg |
| 3. | Magnesium Stearate | 4.0 mg |

Procedure

1. Blend 1, 2 and 3.
2. Mill this blend and blend again.
3. This milled blend is then filled into #1 hard gelatin capsules.

| | Tablets | |
|---|---|---|
| | Ingredients | Mg./Tab. |
| 1. | Active ingredient | 10.0 mg |
| 2. | Corn Starch | 20.0 mg |
| 3. | Alginic acid | 20.0 mg |
| 4. | Sodium alginate | 20.0 mg |
| 5. | Magnesium Stearate | 1.3 mg |

Procedure

1. Blend 1, 2, 3 and 4.
2. Add sufficient water portionwise to the blend from Step #1 with careful stirring after each addition. Such additions of water and stirring continue until the mass is of consistency to permit its conversion to wet granules.

3. The wet mass is converted to granules by passing it through the oscillating granulator, using 8 mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | | |
|---|---|---|
| Ingredient | | Per ml. |
| 1. Active ingredient | | 1.0 mg |
| 2. pH 4.0 Buffer solution | q.s. to | 1.0 ml |

Procedure

1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | | |
|---|---|---|
| Ingredient | | Per ml. |
| 1. Active ingredient | | 5.0 mg |
| 2. Isotonic Buffer solution 4.0 | q.s. to | 1.0 ml |

Procedure

1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
|---|---|
| Ingredient | Per Supp. |
| 1. Active ingredient | 10.0 mg |
| 2. Polyethylene Glycol 1000 | 1350.0 mg |
| 3. Polyethylene Glycol 4000 | 450.0 mg |

Procedure

1. Melt 2 and 3 together and stir until uniform.
2. Dissolve #1 in the molten mass from step #1 and stir until uniform.
3. Pour the molten mass from step #2 into suppository molds and chill.
4. Remove the suppositories from molds and wrap.

Various modifications and equivalents will be apparent to one skilled in the art and may be made in the compounds, methods of treatment and compositions of the present invention without departing from the spirit or scope thereof, and it is therefore to be understood that the invention is to be limited only by the scope of the appended claims.

What is claimed is:

1. A cyclic carbamate derivative, substituted on one of the ring carbon atoms by a 4-[(bis-aryl)-hydroxymethyl]-1-piperidinalkyl radical, selected from a group having the formula:

$$Ar-\underset{Ar^1}{\underset{|}{C}}(OH)-\text{piperidine}-N-alk-(CH_2)_m-N-R, \text{ with } (R^1)_{0-2} \text{ and carbamate } O-C(=O)$$

wherein

R is selected from hydrogen, loweralkyl, cycloalkyl having 3–9 carbon atoms, phenyl,

[phenyl ring with $(X)_{1-3}$ substituents], phenyl-loweralkyl or

[phenyl ring with $(Y)_{1-3}$ substituents], loweralkyl;

Ar and $Ar^1$ are selected from phenyl,

[phenyl ring with $(Z)_{1-3}$ substituents], or 2,3 or 4 pyridinyl radicals;
"alk" is a straight or branched hydrocarbon chain containing 1–8 carbon atoms;
$R^1$ is loweralkyl substituted for hydrogen on a ring carbon;
m is 1 to 4;
X, Y and Z are selected from halogen, loweralkyl, loweralkoxy or trifluoromethyl and when more than 1, may be the same or different;
optical isomers thereof, or a pharmaceutically acceptable acid addition salt thereof.

2. The compound of claim 1 which is 5-[2-[4-[bis(4-fluorophenyl)hydroxymethyl]-1-piperidinyl]ethyl]-3-methyl-2-oxazolidinone or a pharmaceutically acceptable acid addition salt thereof.

3. The compound of claim 1 which is 5-[2-[4-[bis(4-fluorophenyl)hydroxymethyl]-1-piperidinyl]ethyl]-3-methyl-2-oxazolidinone or a pharmaceutically acceptable salt thereof.

4. The compound of claim 1 which is 5-[2-[4-bis(4-methylphenyl)hydroxymethyl]-1-piperidinyl]ethyl]-3-methyl-2-oxazolidinone or a pharmaceutically acceptable acid addition salt thereof.

5. The compound of claim 1 which is S-(−)-5-[2-[4-[bis(4-fluorophenyl)hydroxymethyl]-1-piperidinyl]ethyl]-3-methyl-2-oxazolidinone or a pharmaceutically acceptable acid addition salt thereof.

6. The compound of claim 1 which is R-(+)-5-[2-[4-[bis(4-fluorophenyl)hydroxymethyl]-1-piperidinyl]ethyl-3-methyl-2-oxazolidinone or a pharmaceutically acceptable acid addition salt thereof.

7. The compound of claim 1 which is 5-[2-[4-[bis(4-methoxyphenyl)hydroxymethyl]-1-piperidinyl]ethyl]-3- methyl-2-oxazolidinone or a pharmaceutically acceptable acid addition salt thereof.

8. The compound of claim 1 which is 5-[2-[4-[bis(4-fluorophenyl)hydroxymethyl)-1-piperidinyl]ethyl]-3-phenyl-2-oxazolidinone or a pharmaceutically acceptable acid addition salt thereof.

9. The compound of claim 1 which is 5-[3-[4-[bis(4-fluorophenyl)hydroxymethyl]-1-piperidinyl]propyl]-3-methyl-2-oxazolidinone or a pharmaceutically acceptable acid addition salt thereof.

10. The compound of claim 1 which is 6-[2-[4-[bis(4-fluorophenyl)hydroxymethyl]-1-piperidinyl]ethyl]-3-methyl-tetrahydro-2H-1,3-oxazin-2-one or a pharmaceutically acceptable acid addition salt thereof.

11. The compound of claim 1 which is 5-[[4-[bis(4-fluorophenyl)hydroxymethyl]-1-piperidinyl]methyl]-3-methyl-2-oxazolidinone or a pharmaceutically acceptable acid addition salt thereof.

12. The compound of claim 1 which is 5-[2-[4-[bis(4-fluorophenyl)hydroxymethyl]-1-piperidinyl]ethyl]-3-phenyl-methyl-2-oxazolidinone or a pharmaceutically acceptable acid addition salt thereof.

13. The compound of claim 1 which is 5-[2-[4-[bis(4-fluorophenyl)hydroxymethyl]-1-piperidinyl]ethyl]-3-phenyl-2-oxazolidinone or a pharmaceutically acceptable acid addition salt thereof.

14. The compound of claim 1 which is 5-[2-[4-[bis(4-fluorophenyl)hydroxymethyl]-1-piperidinyl]ethyl]-3-ethyl-2-oxazolidinone or a pharmaceutically acceptable acid addition salt thereof.

15. The compound of claim 1 which is 5-[2-[4-[bis(4-fluorophenyl)hydroxymethyl]-1-piperidinyl]ethyl]-3-(1-methylethyl)-2-oxazolidinone or a pharmaceutically acceptable salt thereof.

16. A method of inhibiting Type 1 allergic response in a living animal which comprises administering to said animal in need thereof an effective amount of a compound selected from the group having the formula:

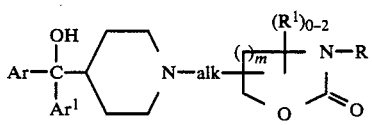

wherein;

R is selected from hydrogen, loweralkyl, cycloalkyl having 3-9 carbon atoms, phenyl,

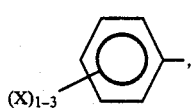

phenyl-loweralkyl or

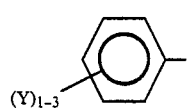

loweralkyl;

Ar and Ar$^1$ are selected from phenyl,

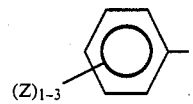

or 2,3 or 4 pyridinyl radicals;

"alk" is a straight or branched hydrocarbon chain containing 1-8 carbons;

R$^1$ is loweralkyl substituted for hydrogen on a ring carbon;

m is 1 to 4;

X, Y and Z are selected from halogen, loweralkyl, loweralkoxy or trifluoromethyl and when more than one, may be the same or different;

optical isomers thereof or a pharmaceutically acceptable acid addition salt thereof.

17. The method of claim 16 wherein the compound is 5-[2-[4-[bis(4-fluorophenyl)hydroxymethyl]-1-piperidinyl]ethyl]-3-methyl-2-oxazolidinone or a pharmaceutically acceptable acid addition salt thereof.

18. The method of claim 16 wherein the compound is 5-[2-[4-[bis(4-fluorophenyl)hydroxymethyl]-1-piperidinyl]ethyl]-3-methyl-2-oxazolidinone or a pharmaceutically acceptable salt thereof.

19. The method of claim 16 wherein the compound is 5-[2-[4-[bis(4-methylphenyl)hydroxymethyl]-1-piperidinyl]ethyl]-3-methyl-2-oxazolidinone or a pharmaceutically acceptable acid addition salt thereof.

20. The method of claim 16 wherein the compound is S-(−)-5-[2-[4-[bis(4-fluorophenyl)hydroxymethyl]-1-piperidinyl]ethyl]-3-methyl-2-oxazolidinone or a pharmaceutically acceptable acid addition salt thereof.

21. The method of claim 16 wherein the compound is R-(+)-5-[2-[4-[bis(4-fluorophenyl)hydroxymethyl]-1-piperidinyl]ethyl -3-methyl-2-oxazolidinone or a pharmaceutically acceptable acid addition salt thereof.

22. The method of claim 16 wherein the compound is 5-[2-[4-[bis(4-methoxyphenyl)hydroxymethyl]-1-piperidinyl]ethyl]-3-methyl-2-oxazolidinone or a pharmaceutically acceptable acid addition salt thereof.

23. The method of claim 16 wherein the compound is 5-[2-[4-[bis(4-fluorophenyl)hydroxymethyl)-1-piperidinyl]ethyl]-3-phenyl-2-oxazolidinone or a pharmaceutically acceptable acid addition salt thereof.

24. The method of claim 16 which is 5-[3-[4-[bis(4-fluorophenyl)hydroxymethyl]-1-piperidinyl]propyl]-3-methyl-2-oxazolidinone or a pharmaceutically acceptable acid addition salt thereof.

25. The method of claim 16 wherein the compound is 6-[2-[4-[bis(4-fluorophenyl)hydroxymethyl]-1-piperidinyl]ethyl]-3-methyl-tetrahydro-2H-1,3-oxazin-2-one or a pharmaceutically acceptable acid addition salt thereof.

26. The method of claim 16 wherein the compound is 5-[[4-[bis(4-fluorophenyl)hydroxymethyl]-1-piperidinyl]methyl]-3-methyl-2-oxazolidinone or a pharmaceutically acceptable acid addition salt thereof.

27. The method of claim 16 wherein the compound is 5-[2-[4-[bis(4-fluorophenyl)hydroxymethyl]-1-piperidinyl]ethyl]-3-phenylmethyl-2-oxazolidinone or a pharmaceutically acceptable acid addition salt thereof.

28. The method of claim 16 wherein the compound is 5-[2-[4-[bis(4-fluorophenyl)hydroxymethyl]-1-piperidinyl]ethyl]-3-phenyl-2-oxazolidinone or a pharmaceutically acceptable acid addition salt thereof.

29. The method of claim 16 wherein the compound is 5-[2-[4-[bis(4-fluorophenyl)hydroxymethyl]-1-piperidinyl]ethyl]-3-ethyl-2-oxazolidinone or a pharmaceutically acceptable acid addition salt thereof.

30. The method of claim 16 wherein the compound is 5-[2-[4-[bis-fluorophenyl)hydroxymethyl]-1-piperidinyl]ethyl]-3-(1-methyl-ethyl)-2-oxazolidinone or a pharmaceutically acceptable salt thereof.

31. A method of countering the effects of histamine in a living animal which comprises administering to said animal in need thereof an effective amount of a compound selected from the group having the formula:

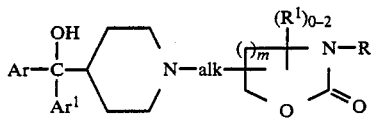

wherein;
R is selected from hydrogen, loweralkyl, cycloalkyl having 3–9 carbon atoms, phenyl,

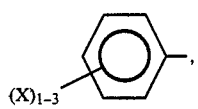

phenyl-loweralkyl or

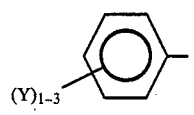

loweralkyl;
Ar and Ar¹ are selected from phenyl,

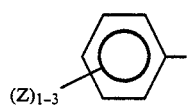

or 2, 3 or 4 pyridinyl radicals;
"alk" is a straight or branched hydrocarbon chain containing 1–8 carbons;
R¹ is loweralkyl substituted for hydrogen on a ring carbon;
m is 1 to 4;
X, Y and Z are selected from halogen, loweralkyl, loweralkoxy or trifluoromethyl and when more than one, may be the same or different;
optical isomers thereof or a pharmaceutically acceptable acid addition salt thereof.

32. The method of claim 31 wherein the compound is 5-[2-[4-[bis(4-fluorophenyl)hydroxymethyl]-1-piperidinyl]ethyl]-3-methyl-2-oxazolidinone or a pharmaceutically acceptable acid addition salt thereof.

33. The method of claim 31 wherein the compound is 5-[2-[4-[bis(4-fluorophenyl)hydroxymethyl-1-piperidinyl]ethyl]-3-methyl-2-oxazolidinone or a pharmaceutically acceptable salt thereof.

34. The method of claim 31 wherein the compound is 5-[2-[4-[bis(4-methylphenyl)hydroxymethyl]-1-piperidinyl]ethyl]-3-methyl-2-oxazolidinone or a pharmaceutically acceptable acid addition salt thereof.

35. The method of claim 31 wherein the compound is S-(−)-5-[2-[4-[bis(4-fluorophenyl)hydroxymethyl]-1-piperidinyl]ethyl]-3-methyl-2-oxazolidinone or a pharmaceutically acceptable acid addition salt thereof.

36. The method of claim 31 wherein the compound is R-(+)-5-[2-[4-[bis(4-fluorophenyl)hydroxymethyl]-1-piperidinyl]ethyl-3-methyl-2-oxazolidinone or a pharmaceutically acceptable acid addition salt thereof.

37. The method of claim 31 wherein the compound is 5-[2-[4-[bis(4-methoxyphenyl)hydroxymethyl]-1-piperidinyl]ethyl]-3-methyl-2-oxazolidinone or a pharmaceutically acceptable acid addition salt thereof.

38. The method of claim 31 wherein the compound is 5-[2-[4-[bis(4-fluorophenyl)hydroxymethyl)-1-piperidinyl]ethyl-3-phenyl-2-oxazolidinone or a pharmaceutically acceptable acid addition salt thereof.

39. The method of claim 31 wherein the compound is 5-[3-[4-[bis(4-fluorophenyl)hydroxymethyl]-1-piperidinyl]propyl]-3-methyl-2-oxazolidinone or a pharmaceutically acceptable acid addition salt thereof.

40. The method of claim 31 wherein the compound is 6-[2-[4-[bis(4-fluorophenyl)hydroxymethyl]-1-piperidinyl]ethyl]-3-methyl-tetrahydro-2H-1,3-oxazin-2-one or a pharmaceutically acceptable acid addition salt thereof.

41. The method of claim 31 wherein the compound is 5-[[4-[bis(4-fluorophenyl)hydroxymethyl]-1-piperidinyl]methyl]-3-methyl-2-oxazolidinone or a pharmaceutically acceptable acid addition salt thereof.

42. The method of claim 31 wherein the compound is 5-[2-[4-[bis(4-fluorophenyl)hydroxymethyl]-1-piperidinyl]ethyl]-3-phenylmethyl-2-oxazolidinone or a pharmaceutically acceptable acid addition salt thereof.

43. The method of claim 31 wherein the compound is 5-[2-[4-[bis(4-fluorophenyl)hydroxymethyl]-1-piperidinyl]ethyl]-3-phenyl-2-oxazolidinone or a pharmaceutically acceptable acid addition salt thereof.

44. The method of claim 31 wherein the compound is 5-[2-[4-[bis(4-fluorophenyl)hydroxymethyl]-1-piperidinyl]ethyl]-3-ethyl-2-oxazolidinone or a pharmaceutically acceptable acid addition salt thereof.

45. The method of claim 31 wherein the compound is 5-[2-[4-[bis(4-fluorophenyl)hydroxymethyl]-1-piperidinyl]ethyl]-3-(1-methyl-ethyl)-2-oxazolidinone or a pharmaceutically acceptable salt thereof.

46. A pharmaceutical composition suitable for countering the effects of histamine and/or for inhibiting Type 1 allergic response in a living animal comprising a) an effective amount of a compound selected from the group having the formula:

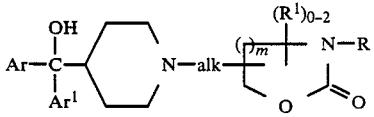

wherein;
R is selected from hydrogen, loweralkyl, cycloalkyl having 3–9 carbon atoms, phenyl,

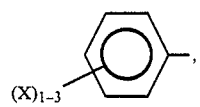

phenyl-loweralkyl or

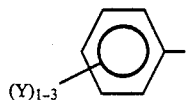

loweralkyl;

Ar and Ar¹ are selected from phenyl,

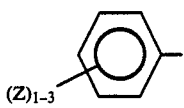

or 2, 3 or 4 pyridinyl radicals;

"alk" is a straight or branched hydrocarbon chain containing 1–8 carbon atoms;

$R^1$ is loweralkyl substituted for hydrogen on a ring carbon;

m is 1 to 4;

X, Y and Z are selected from halogen, loweralkyl, loweralkoxy or trifluoromethyl and when more than one, may be the same or different;

optical isomers thereof or a pharmaceutically acceptable acid addition salt thereof and, (b) a pharmaceutical carrier therefor.

47. The pharmaceutical composition of claim 46 wherein the compound is 5-[2-[4-[bis(4-fluorophenyl)-hydroxymethyl]-1-piperidinyl]ethyl]-3-methyl-2-oxazolidinone or a pharmaceutically acceptable acid addition salt thereof.

48. The pharmaceutical composition of claim 46 wherein the compound is 5-[2-[4-[bis(4-fluorophenyl)-hydroxymethyl-1-piperidinyl]ethyl]-3-methyl-2-oxazolidinone or a pharmaceutically acceptable salt thereof.

49. The pharmaceutical composition of claim 46 wherein the compound is 5-[2-[4-[bis(4-methylphenyl)-hydroxymethyl]-1-piperidinyl]ethyl]-3-methyl-2-oxazolidinone or a pharmaceutically acceptable acid addition salt thereof.

50. The pharmaceutical composition of claim 46 wherein the compound is S-(−)-5-[2-[4-[bis(4-fluorophenyl)hydroxymethyl]-1-piperidinyl]ethyl]-3-methyl-2-oxazolidinone or a pharmaceutically acceptable acid addition salt thereof.

51. The pharmaceutical composition of claim 46 wherein the compound is R-(+)-5-[2-[4-[bis(4-fluorophenyl)hydroxymethyl]-1-piperidinyl]ethyl-3-methyl-2-oxazolidinone or a pharmaceutically acceptable acid addition salt thereof.

52. The pharmaceutical composition of claim 46 wherein the compound is 5-[2-[4-[bis(4-methoxyphenyl)hydroxymethyl]-1-piperidinyl]ethyl]-3-methyl-2-oxazolidinone or a pharmaceutically acceptable acid addition salt thereof.

53. The pharmaceutical composition of claim 46 wherein the compound is 5-[2-[4-[bis(4-fluorophenyl)-hydroxymethyl]-1-piperidinyl]ethyl]-3-phenyl-2-oxazolidinone or a pharmaceutically acceptable acid addition salt thereof.

54. The pharmaceutical composition of claim 46 wherein the compound is 5-[3-[4-[bis(4-fluorophenyl)-hydroxymethyl]-1-piperidinyl]propyl]-3-methyl-2-oxazolidinone or a pharmaceutically acceptable acid addition salt thereof.

55. The pharmaceutical composition of claim 46 wherein the compound is 6-[2-[4-[bis(4-fluorophenyl)-hydroxymethyl]-1-piperidinyl]ethyl]-3-methyl-tetrahydro-2H-1,3-oxazin-2-one or a pharmaceutically acceptable acid addition salt thereof.

56. The pharmaceutical composition of claim 46 wherein the compound is 5-[[4-[bis(4-fluorophenyl)hydroxymethyl]-1-piperidinyl]methyl]-3-methyl-2-oxazolidinone or a pharmaceutically acceptable acid addition salt thereof.

57. The pharmaceutical composition of claim 46 wherein the compound is 5-[2-[4-[bis(4-fluorophenyl)-hydroxymethyl]-1-piperidinyl]ethyl]-3-phenylmethyl-2-oxazolidinone or a pharmaceutically acceptable acid addition salt thereof.

58. The pharmaceutical composition of claim 46 wherein the compound is 5-[2-[4-[bis(4-fluorophenyl)-hydroxymethyl]-1-piperidinyl]ethyl]-3-phenyl-2-oxazolidinone or a pharmaceutically acceptable acid addition salt thereof.

59. The pharmaceutical composition of claim 46 wherein the compound is 5-[2-[4-[bis(4-fluorophenyl)-hydroxymethyl]-1-piperidinyl]ethyl]-3-ethyl-2-oxazolidinone or a pharmaceutically acceptable acid addition salt thereof.

60. The pharmaceutical composition of claim 46 wherein the compound is 5-[2-[4-[bis(4-fluorophenyl)-hyxroxymethyl]-1-piperidinyl]ethyl]-3-(1-methylethyl)-2-oxazolidinone or a pharmaceutically acceptable salt thereof.

* * * * *